(12) United States Patent
Ehrick

(10) Patent No.: US 8,415,648 B2
(45) Date of Patent: Apr. 9, 2013

(54) METHOD OF DETERMINATION OF GLASS SURFACE SHAPES AND OPTICAL DISTORTION BY REFLECTED OPTICAL IMAGING

(75) Inventor: Michael R. Ehrick, Toledo, OH (US)

(73) Assignee: Pilkington Group Limited, Lathom (GB)

( * ) Notice: Subject to any disclaimer, the term of this patent is extended or adjusted under 35 U.S.C. 154(b) by 0 days.

(21) Appl. No.: 12/735,495

(22) PCT Filed: Feb. 13, 2009

(86) PCT No.: PCT/US2009/000950
§ 371 (c)(1),
(2), (4) Date: Jul. 21, 2010

(87) PCT Pub. No.: WO2009/102490
PCT Pub. Date: Aug. 20, 2009

(65) Prior Publication Data
US 2010/0309328 A1 Dec. 9, 2010

Related U.S. Application Data

(60) Provisional application No. 61/065,999, filed on Feb. 15, 2008.

(51) Int. Cl.
*G01N 21/86* (2006.01)

(52) U.S. Cl.
USPC ............... 250/559.07; 250/559.01; 250/221; 356/239.1; 356/601; 356/610

(58) Field of Classification Search .................. 250/221, 250/559.01, 559.04, 559.05, 559.07, 559.19, 250/559.22; 356/239.1, 239.7, 600–602, 356/605, 610, 630
See application file for complete search history.

(56) References Cited

U.S. PATENT DOCUMENTS 4,853,777 A   8/1989   Hupp
(Continued)

FOREIGN PATENT DOCUMENTS

EP    1 906 139 A1    4/2008
WO   WO 2007/010875 A1   1/2007

OTHER PUBLICATIONS

Joaquim Salvi et al; Pattern condification strategies in structured light systems; 2003 Pattern Recognition Society; 2004; pp. 827-849; Pattern Recognition; vol. 37, No. 4, Apr. 1, 2004; pp. 827-849; Elsevier, GB; XP004491495.

(Continued)

*Primary Examiner* — Kevin Pyo
(74) *Attorney, Agent, or Firm* — Marshall & Melhorn, LLC

(57) ABSTRACT

A non-contact, opto-electronic method to determine glass surface shape involves pattern projection in reflection from a screen. The pattern is formed of black and white or coloured squares with a central reference pattern taken as origin of the x-y axes in the subsequent quantitative analysis of the optical distortion in formed glass sheets or panels.

18 Claims, 7 Drawing Sheets

U.S. PATENT DOCUMENTS

| | | |
|---|---|---|
| 5,067,817 A | 11/1991 | Glenn |
| 5,085,516 A | 2/1992 | Bertrand et al. |
| 5,568,258 A | 10/1996 | Uemura et al. |
| 5,835,223 A * | 11/1998 | Zwemer et al. ............... 356/600 |
| 6,122,065 A | 9/2000 | Gauthier |
| 6,376,829 B1 | 4/2002 | Okugawa |
| 6,433,353 B2 | 8/2002 | Okugawa |
| 7,430,049 B2 | 9/2008 | Bertin-Mourot et al. |
| 7,471,383 B2 | 12/2008 | Ehrick |
| 7,589,844 B2 * | 9/2009 | Hirata et al. .................. 356/601 |

OTHER PUBLICATIONS

O.A. Skydan et al; 3D shape measurement of automotive glass by using a fringe reflection technique; Measurement Science and Technology, Institute of Physics Publishing; vol. 18, No. 1; Jan. 1, 2007; Bristol, GB; pp. 106-114; XP020118464.

* cited by examiner

METHOD OF DETERMINATION OF GLASS SURFACE SHAPES AND OPTICAL DISTORTION BY REFLECTED OPTICAL IMAGING

RELATED APPLICATIONS

This application is claiming the benefit, under 35 U.S. C. 119(e), of the provisional application filed Feb. 15, 2008 under 35 U.S. C. 111(b), which was granted Serial No. 61/065,999.

BACKGROUND

The present invention relates to a non-contact, opto-electronic method of determining the surface shape of a curved, formed sheet of glass to a useful precision, and for analyzing optical distortion occurring in such formed glass sheets.

Glass forming processes, typically, involve heating a glass sheet or panel to, or near, its softening temperature, and then forming the glass to a desired configuration by, for example, gravity bending or press bending. Such heating and forming operations have the potential to create physical and optical defects in the glass sheet or panel, for example deviation from the desired configuration and/or optical distortion. Particular types of non-obvious physical glass defects may cause problems with subsequent processing of the formed glass sheet and/or may pose difficulties when, for example, such formed glass sheet is a vehicle window, and it is being installed in a vehicle body opening at a vehicle assembly plant. Reflected optical distortion may also be unacceptable to vehicle manufacturers, and may be annoying to vehicle drivers/passengers. It would be desirable to have an automated system to determine glass surface shape as well as being capable of objectively assessing optical distortion in shaped glass sheets or panels, in order to minimize formed glass sheets having such non-obvious physical and/or optical defects, enter the stream of commerce.

Automated systems purported to detect and measure physical and optical defects in formed glass sheets or panels are the subject of many U.S. patents. For example:

U.S. Pat. No. 5,067,817 describes a method and apparatus for measuring the curvature and profile of a reflective test surface by simultaneous measurement of slope at two closely spaced points on the test surface.

U.S. Pat. No. 5,085,516 describes a method and apparatus for comparing the shape of the edges of a curved object being monitored, with the shape of standard curved object. An application of the method and apparatus is said to be monitoring of window panels in the automobile industry.

U.S. Pat. No. 5,568,258 describes a method of measuring distortion of a transmitting beam, characterized in that, a transmitting beam is emitted from a beam generator and projected onto a screen as a bright spot, the bright spot is scanned over the surface of the screen, and distortion of the transmitting beam is measured on the basis of a distance between a first location of the bright spot at a first time when the transmitting beam is incident on a beam receiving device, in a specified incident direction, upon being transmitted through a measured body, and a second location of the bright spot on the screen at a second time when the transmitting beam is incident on the beam receiving device in the specified incident direction, but the transmitting beam is not transmitted through the measured body.

U.S. Pat. No. 6,122,065 describes an apparatus and method for detecting surface defects on an article freely standing on a conveyor, which generates profile trace data corresponding to profile trace at a cross-section of the article. A surface shape inspection unit comprising an optical ranging system using a laser and a camera for obtaining the profile trace data through triangulation-based derivation techniques.

U.S. Pat. No. 4,853,777 describes a system to quantitatively determine the short-term and long-term waviness of a smooth surface by impinging light radiation, namely laser light, onto the surface, detecting the resultant light image and mathematically processing the subject light image.

U.S. Pat. Nos. 6,376,829 and 6,433,353 describe a method and apparatus for detecting front surface irregularities in a glass plate. More specifically, the method described involves irradiating a beam of light toward a surface of a transparent plate at an angle of incidence between 86° and 89°, or 60° to 89° after such light beam is polarized ("P" or "S"-polarized) by a polarizing element between the light beam source and the transparent plate. A reflected image from a front surface of the transparent plate is then projected on a screen, is inspected by one of several possible methods, whereby density signals said to be representative of the reflected image are analyzed to calculate the irregularities present on the surface of the transparent plate.

SUMMARY OF THE INVENTION

The present invention is directed to a non-contact, opto-electronic method of determining the surface shape of a curved, formed sheet of glass to a useful precision, for quantitatively analyzing reflected optical distortion in such formed glass sheets and doing so in a manner whereby the analysis of non-obvious physical and/or optical defects in individual glass sheets provides a basis to effect changes in, for example, a glass shaping production process.

The method of the present invention utilizes a visible light source to illuminate a selectively oriented, flat or curved, rigid surface having a pattern disposed thereon, for example a grid pattern of, alternating dark and light squares, or multi-colored squares, or a pattern of spatially separated geometric shapes. The light from the visible light source is reflected from the selectively oriented, rigid patterned surface onto a pre-positioned, essentially horizontal surface, on which surface a formed glass sheet having a major, convex surface facing outward, has been precisely oriented. The pattern reflected from the illuminated vertical, rigid patterned surface is then visible in reflection on the major convex surface of the shaped glass sheet. The image of the pattern visible on the surface of the shaped glass sheet is reflected into a pre-positioned opto-electronic device, for example, a digital camera, which captures the image, digitally, for transfer to a computer containing one or more algorithms capable of analyzing desired parameters of the digital image transferred from the opto-electronic device.

BRIEF DESCRIPTION OF THE DRAWINGS

Other features and advantages of the invention will be readily apparent from the following detailed description when taken in conjunction with the accompanying drawings.

DETAILED DESCRIPTION OF THE INVENTION

The present invention is directed to a non-contact, opto-electronic method of determining the surface shape of a curved, formed sheet of glass to a useful precision and also to quantitatively analyzing reflected optical distortion in such formed glass sheets.

The method of the present invention is thought to be particularly useful where such analysis is done repeatedly in, for example, a glass quality assessment laboratory or directly as a component of a glass shaping production process. The method of the present invention is implemented by utilizing a number of components integrated into an effective, yet relatively simple system.

Figure 1:
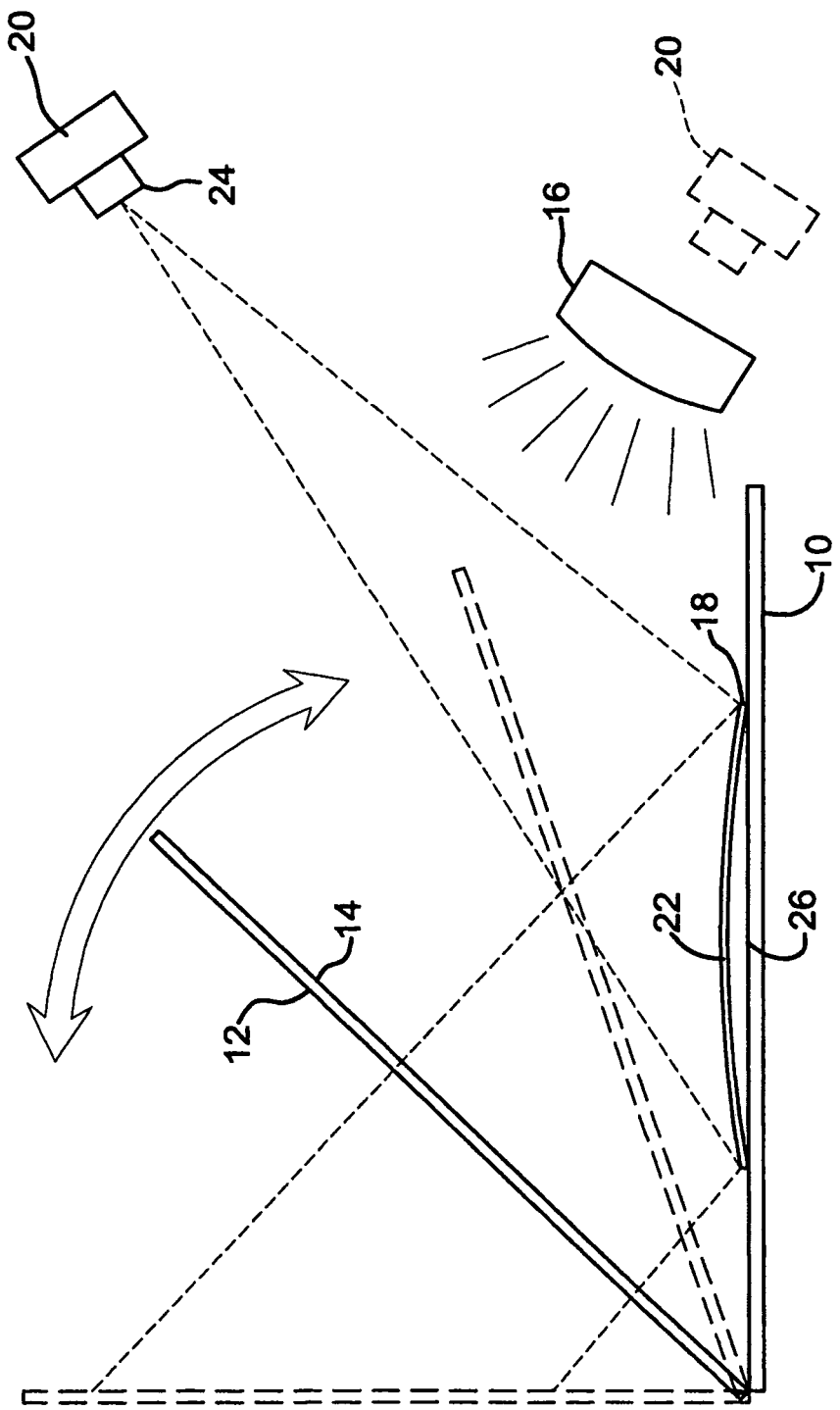
FIG. 1 shows a schematic representation of the imaging/analytical system of the present invention with the selectively oriented rigid surface having a pattern thereon in several possible orientations.

As shown in FIG. 1, a rigid horizontal surface 10, such as a registration table or a surface in a glass sheet transport system is placed in predetermined proximity to a selectively oriented, flat or curved, rigid surface 12, with a pattern 14 disposed thereon. For purposes of this application, "selectively oriented" means that the flat or curved rigid surface 12 on which the pattern is disposed may be oriented in any orientation from perpendicular to parallel (but separated from) the rigid horizontal surface 10. Preferably, the selectively oriented surface is at an angle of about 45° relative to the rigid horizontal surface 10. For example, a grid pattern of alternating black and white squares or a pattern of multi-colored squares may be utilized in connection with the invention. Preferably, a pattern of a plurality of geometric shapes such as circles or squares, separated by a predetermined distance from one another is utilized in connection with the invention. While not critical, the typical sizes of the subject horizontal and selectively oriented surfaces are 36 in.×72 in. and 72 in.×72 in., respectively. A source of visible light 16 is positioned in predetermined proximity to the selectively oriented, flat or curved, rigid surface 12, typically within 8-10 feet of the selectively oriented surface 12. The source of visible light 16 may be any suitable source, but may preferably be one or more incandescent flood lamps each having an output of, for example, 250 watts (3600 lumens). The light 16 is shown on the patterned selectively oriented surface 12 and is reflected diffusely therefrom onto the horizontal rigid surface 10. The selectively oriented rigid surface 12 could also be lighted from behind the surface with, for example, a pattern of opaque black squares and translucent white squares.

Figure 2:
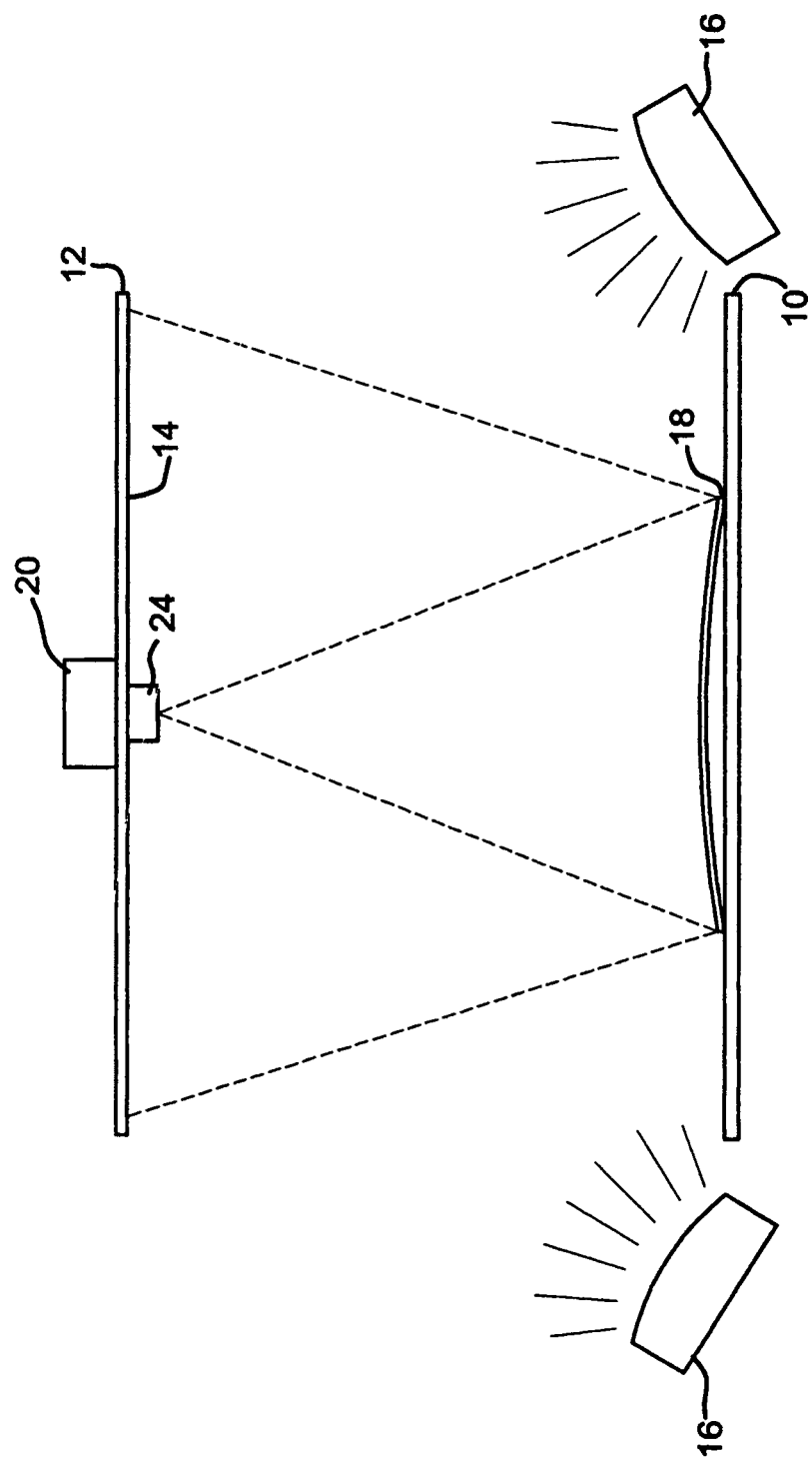
FIG. 2 shows a schematic representation of the imaging/analytical system of the present invention with the rigid surface having a pattern thereon being oriented parallel to the formed sheet of glass.
Figure 4:
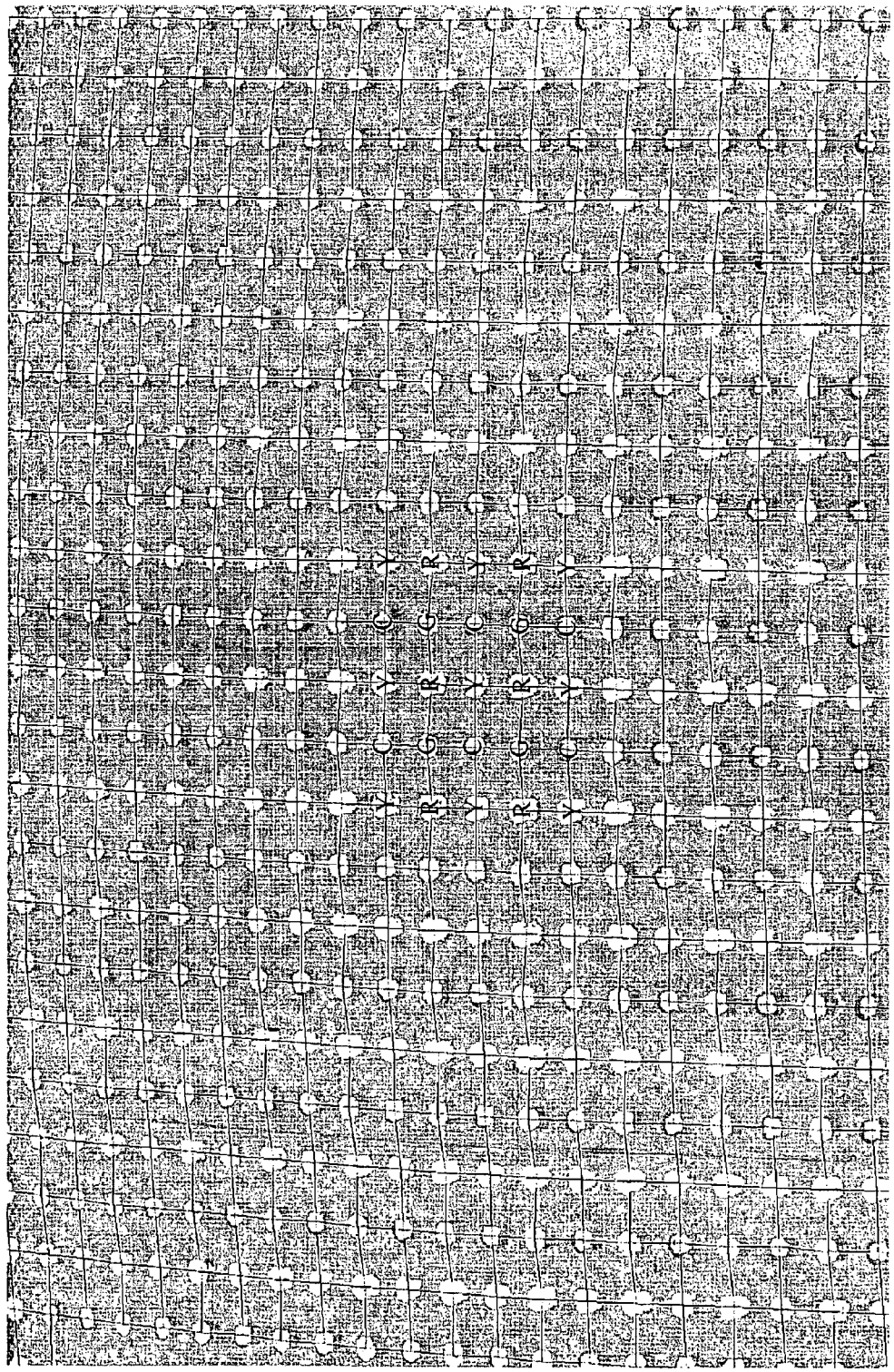
FIG. 4 shows a representative image of a pattern reflected from a glass sheet exhibiting a relatively small amount of deviation from design utilizing the system of the present invention.
Figure 5:
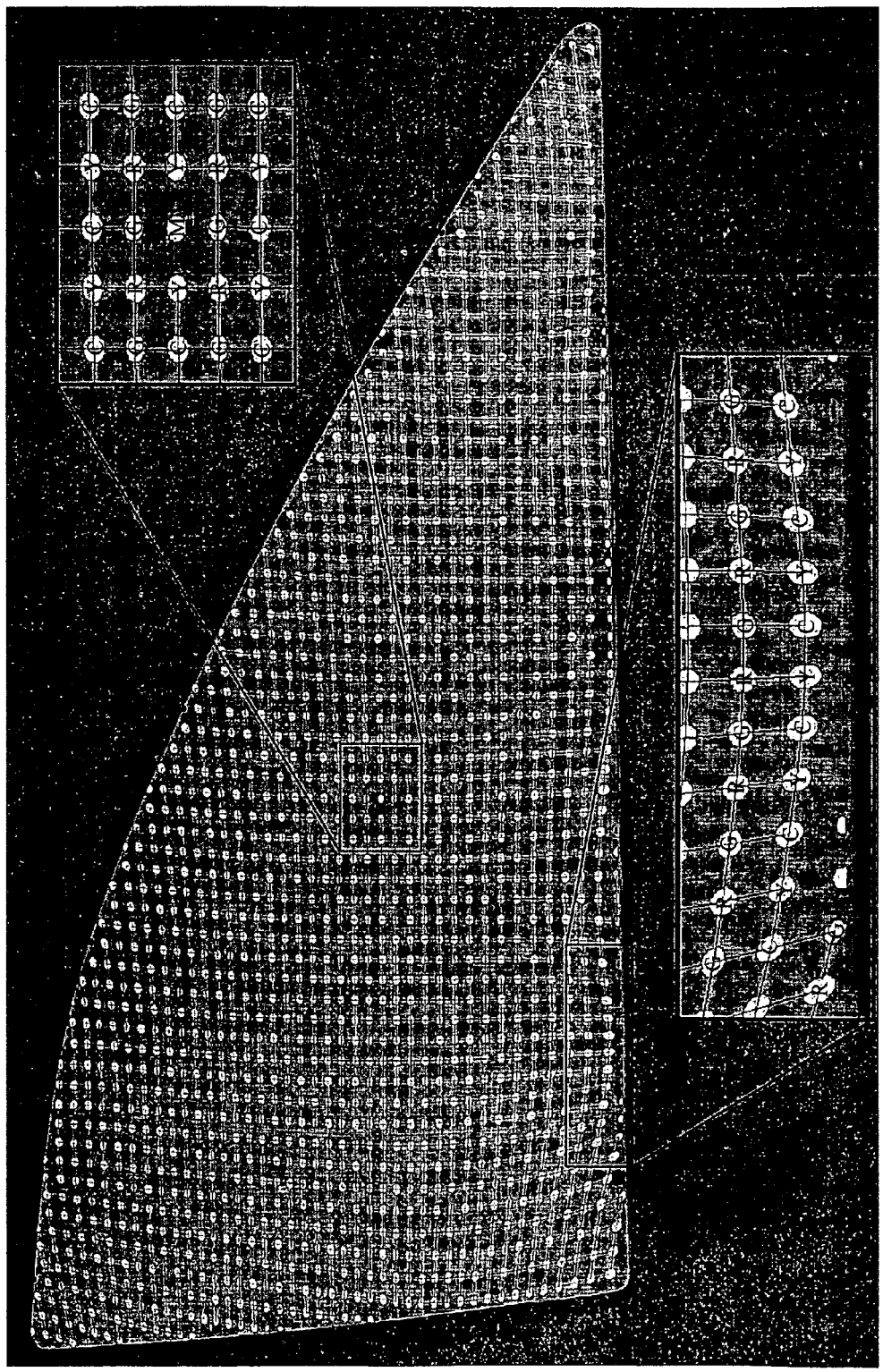
FIG. 5 shows a representative glass sheet exhibiting a reflected pattern which shows some level of distortion in the panel, as detected by the system of the present invention.

A shaped sheet or panel of glass 18, having a major, convex surface facing outward, is precisely oriented on the rigid horizontal surface 10 with respect to the selectively oriented surface 12, oriented at about 45° to the rigid horizontal surface 10 as shown in FIG. 1. Upon proper orientation, the suitable pattern, on the patterned, selectively oriented, surface 12 is reflected onto the major convex surface 22 of the glass sheet or panel 18. The reflected image of the pattern from the selectively oriented surface 12 visible on the major convex surface 22 of the shaped glass sheet 18 (the upper or outer surface), is altered by the curvature of the shaped glass sheet. See FIGS. 2, 4 and 5. The shape of the glass, including any features that create reflected optical distortion, will exert a predictable effect on the reflected image of the grid pattern. The light beams forming the visible image of the pattern on the glass sheet are, primarily reflected into the image capture portion 24 of an opto-electronic device at an angle of incidence of which provides a clearly reflected image from the glass sheet surface to the image capture portion 24 of the image capture device, see for example, FIG. 1. The image capture portion 24 may be the lens of, for example, a digital camera. Other suitable image capture devices 20 could include an analog or digital video camera. The image captured is digitized in the image capture device 20 or another device, and is transmitted by known methods to a suitable computer (not shown). Typically, the image capture device 20 will be positioned so as to receive an optimal amount of the light reflected uniformly from the surface 22 of the shaped glass sheet 18, as shown in FIG. 1. The distance between the shaped glass sheet 18 and the image capture device 20 is preferably 3-12 feet, most preferably between 4 feet and 8 feet. The axis angle of the image capture portion 24 of the image capture device 20 should be set so as to be compatible with the angle of incidence of the light reflected from the shaped glass sheet 18.

Figure 3:
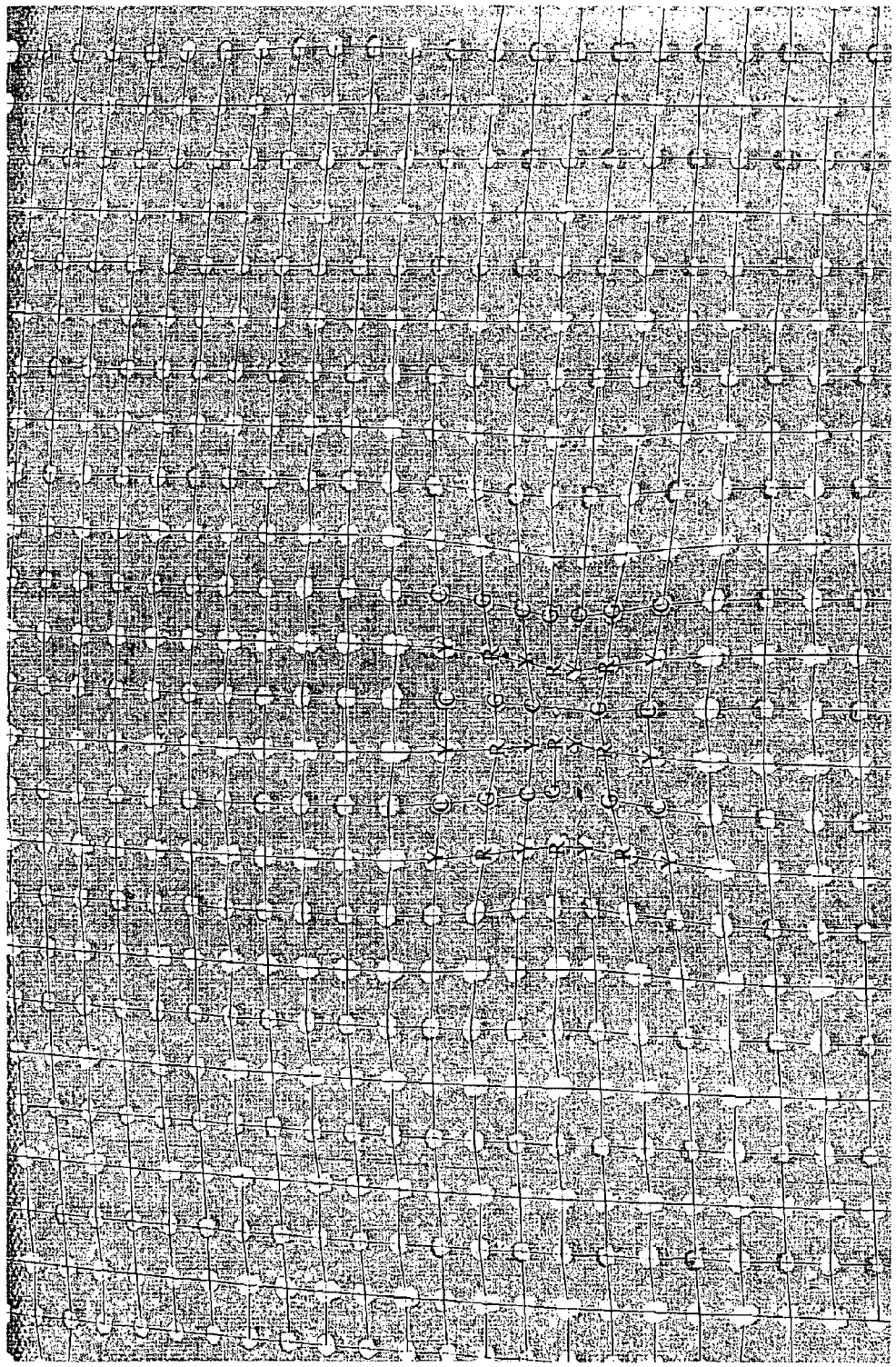
FIG. 3 shows a representative image of a pattern reflected from a glass sheet exhibiting a relatively small absolute deviation from design, concentrated within a very small distance, utilizing the system of the present invention.

The digital image data transmitted to the computer is analyzed by at least one algorithm to measure shape and quantify distortion present in the shaped glass sheet 18. For example, a useful algorithm traces light ray paths from known vertices on the grid pattern, to their (apparent) reflected locations on glass surface (22), to the optical center of the image capture portion 24. Using the law of equal angles of incidence and reflection, the orientation in space of the glass surface (or more properly, the plane tangent to it) at the reflected location on glass surface 22 can be determined. To accomplish this, it is necessary also to know the location in three-dimensional space of the glass surface 22 at every apparent reflected grid vertex. This can be accomplished by integration, starting from the three or more known locations where the glass sheet 18 is supported on the horizontal surface. Alternatively, if the design shape of the glass is known, and the actual shape of the formed glass sheet is assumed to be close to the design shape, the observed difference from the design surface shape can be calculated for every reflected grid vertex. See FIG. 3.

The method of the present invention can be used to determine glass surface shape, and to measure reflected distortion in a shaped glass sheet, in one aspect, by utilizing a grid pattern of alternating dark and light squares or squares of alternating colors.

Existing data suggests that the choice of pattern (i.e., black and white or multi-colored squares) may be influenced by the tint of the glass which is being analyzed. For example, a formed, dark gray glass sheet having a visible light transmittance less than 20% may be more accurately characterized by using any one of a number of patterns, including grid patterns of black and white squares or squares of alternating colors, as well as patterns of spatially separated geometric shapes. This is believed to be true due to the absence of ambiguity caused by second surface reflection. Conversely, a formed light green glass sheet having a visible light transmittance greater than 60% may be more accurately characterized by using a pattern having spatially separated alternating black squares on a white background, or a pattern of spatially separated colored geometric shapes. This is believed to be true due to ambiguity caused by second surface reflection.

A grid pattern of alternating colored squares, in accordance with the present invention, comprises a predetermined number of colored squares, each square being between 1 and 25 mm, preferably about 5 mm, on a side. A center reference square is, for example, white. A pattern of overlapping horizontal and vertical stripes of differing colors, for example red and green, respectively, is adjacent to the reference square. At each location where the vertical and horizontal stripes overlap, the color observed would be the additive color of the horizontal and vertical stripes, in this example yellow, as the additive color of red and green. In void areas between the horizontal and vertical strips, a different color square, for example black, may be utilized. The method of the present invention can identify at least eight different colors, for example, black, white, red, green, blue, cyan, magenta and yellow, however, other colors may also be used. Various combinations of these colors may be utilized in connection with the present invention. Utilizing the grid pattern of different color squares allows the at least one algorithm installed in the computer to "navigate" throughout the grid and to "map" the reflected image on the convex surface of the glass sheet. More particularly, the grid pattern described herein allows the at least one software algorithm to locate the center of the grid, that is the origin or intersection of x and y axes, also referred to herein as the reference square. Different color squares adjacent to the reference square are used to designate different directions to be recognized by the algorithm, for example, cyan equals "up" on the y (vertical) axis, blue equals "right" on the x (horizontal) axis. With this basic information, the algorithm is able to recognize a repeating group of squares of the "direction" colors and transition colors between squares to identify and "plot" horizontal and vertical borders of contiguous squares and thus to "count" squares from the reference square. By this means, the algorithm develops a lattice of points corresponding to corners of squares which, in turn, correspond precisely to known points in a reference, i.e., undistorted pattern. Thus, by knowing or being able to determine (a) the location of a given point in an undistorted image (b) the x-y coordinates of the corresponding point in the reflected (distorted) image, (c) the precise location of the major convex surface 22 of the shaped glass sheet 18 relative to the image capture device 20 and (d) the design shape of the formed glass sheet 18, the at least one algorithm can calculate the inclination of the glass surface (or more accurately, the plane tangent to it) in two dimensions, at each such point. The inclination data can then be differentiated numerically to identify areas where curvatures of the reflected gridlines are changing most rapidly. Waviness in the glass 18 which causes reflected optical distortion can be expressed in terms of the rate of change of surface angle (inclination) over the area converted to, for example, milliradians, in both the x and y directions.

Advantages of the grid of multiple alternating colors include increased ease of analysis due to: (1) determination of grid square boundaries due to use of multiple colors, as compared to use of grids of black or white lines forming intersections of monochrome lines of non-zero width, which are often used in qualitative human visual assessment of reflected optical distortion, as the monochrome lines will be bent and warped in reflection; (2) facilitating location of the origin, or reference square and the cardinal direction; and (3) measurements utilizing the method of the present invention relate directly to the shape of the glass through the inclination in three-dimensional space of the plane tangent to the glass at each identified point on the grid, whereas, in the method described in U.S. Pat. No. 7,471,383 (incorporated by reference herein), defects to be studied must be pre-identified, and the numerical scores produced by that method are sensitive to system geometry and glass location within the field of view of the image capture device; and (4) location of the edges of the shaped glass sheet can be much more easily identified by the algorithm of the present invention, as compared to known methods, by the simple expedient of coloring the rigid horizontal surface on which the shaped glass sheet is placed in a color identifiable by the algorithm, but which has not been used in the color grid pattern.

As previously mentioned herein, rather than utilizing a grid pattern of alternating multiple colored squares to analyze reflected distortion, it has been found, under certain circumstances, to be advantageous to utilize instead, a pattern comprising a plurality of colored geometric shapes, such as circles or squares, preferably disposed on a white background, which shapes are separated from one another by a predetermined distance. (See FIG. 6). Utilization of such patterns of spatially separated geometric shapes has been found to be particularly useful with typical green-tinted automotive glass such as those sold by Pilkington North America, Inc. as EZ KOOL® and EZ EYE™ Patterns of such spatially separated geometric shapes have been found to be preferable to the previously described grid patterns in that so-called "second surface" reflections; that is, generally, the reflection of light from the second major surface 26 of the glass sheet 18, which is most distant from the light source of the system of the present invention. Such second surface reflections, particularly with green glasses, can in the aforementioned grid patterns overlay with first surface reflections to form "mixed" colors which, typically, cannot be accurately characterized by the algorithms of the present invention. The use of the spatially separated geometric shapes has been found to eliminate or, at least, minimize the interference effects of second surface reflections.

Figure 6:
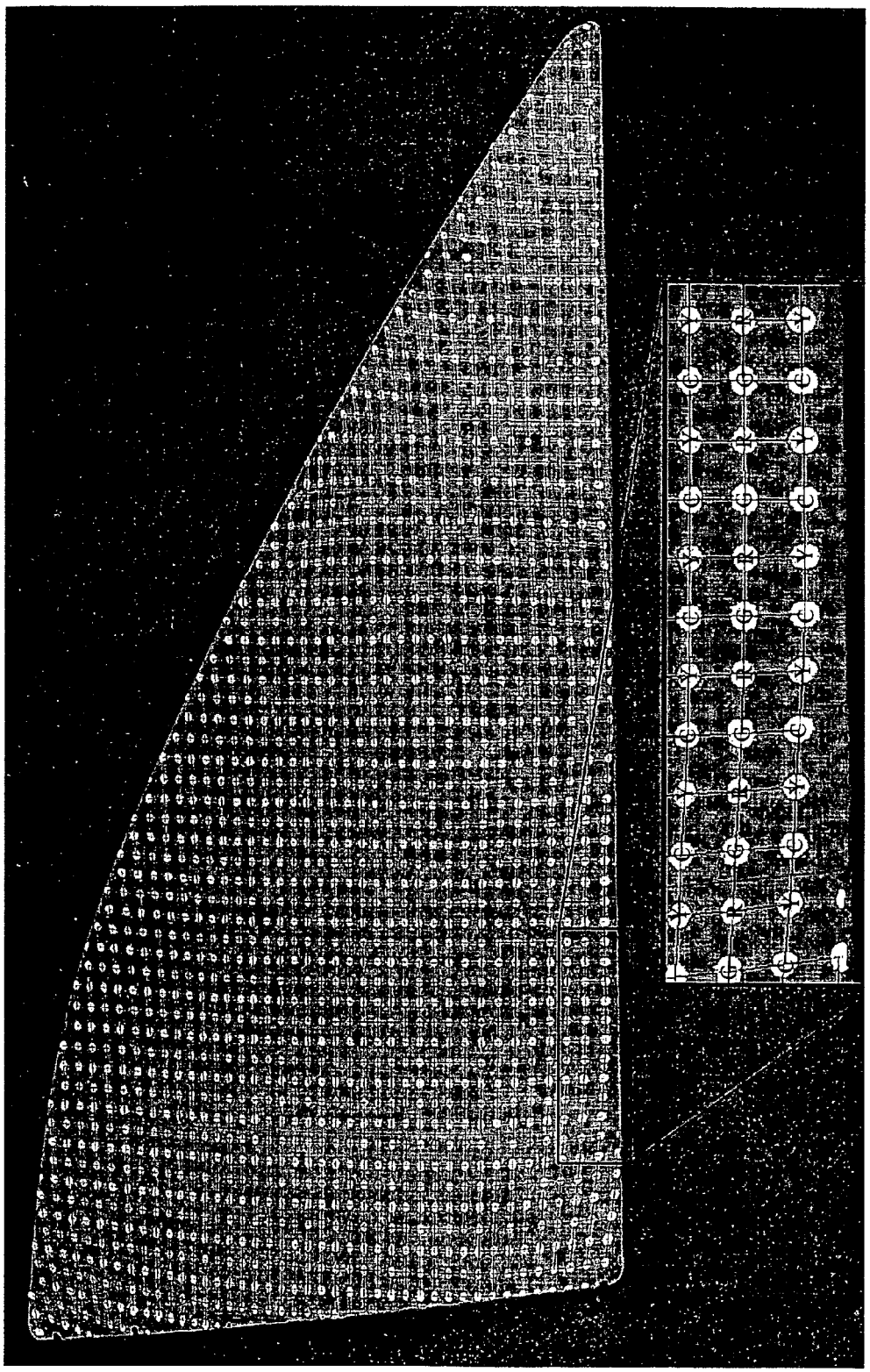
FIG. 6 shows a representative glass panel exhibiting a reflected pattern which shows negligible distortion in the panel, as detected by the system of the present invention.
Figure 7:
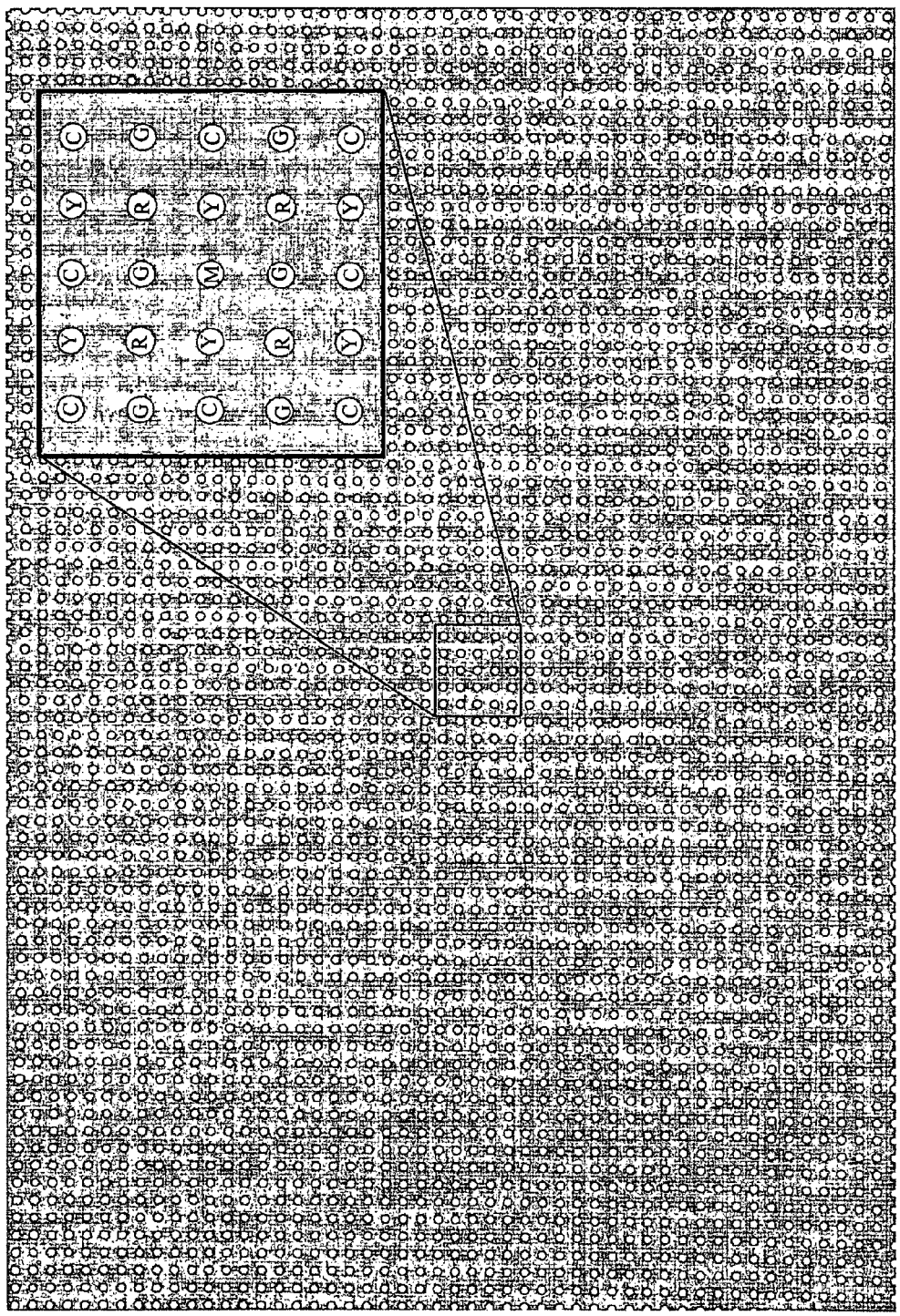
FIG. 7 shows a pattern of non-connected geometric shapes which may be utilized in connection with the present invention.

As with the grid patterns of multiple colored squares, the colors of the spatially separated geometric shapes alternate in predetermined patterns to allow the system to determine a particular location on the first major surface of the shaped glass sheet to be analyzed, as well as to precisely determine the overall shape of the curved glass sheet. It has also been found that the "palette" of colors which can be accurately distinguished by the system of the present invention in connection with the spatially separated geometric shapes differs slightly from the grid pattern of multi-colored squares, preferably comprising black, white, red 30, green 32, cyan 34, magenta 38 and yellow 36, although magenta is preferably used in a limited manner, for example as a single "reference shape" or the origin point of the pattern. A representative pattern is shown in FIGS. 6 and 7. It has also been found to be useful in connection with patterns of spatially separated geometric shapes, based on the application, choose size and spacing of the geometric shapes, as well as to, locally, correct for the apparent shade of white of the background on which the geometric shapes are disposed. Such choices of shape and correction of background can be made for a variety of reasons, including, for example, maximizing the contrast between the geometric shape and the background, minimizing the previously described interference caused by second surface reflections, and the like.

Other potentially useful algorithms include computation of rate of curvature changes in lines formed by connecting vertices from the reflected pattern.

It is anticipated that the present invention will have particular applicability for highly shaped vehicle backlights although analysis of other vehicle glazings such as sidelights and sunroofs is also possible. Use of multiple image capture devices and multiple patterns is within the scope of the invention. As previously noted, the grid pattern of alternating multiple colored squares produces the most accurate results when analyzing darkly tinted glass sheets.

Those skilled in the art of analysis of glass distortion will appreciate that those defects made evident by reflected light are different from defects exposed by use of transmitted light shown through a glass pane. In particular, distortion in glass disclosed by the use of reflected light may be caused by small irregularities in surface curvature made most evident when viewed along, for example, a vehicle window at a low angle of incidence. Such defects in the appearance of the exterior of vehicle glass are of increasing concern to some manufacturers of luxury and near-luxury vehicles.

The present invention has been described in an illustrative manner. Many modifications and variations of the present invention will occur to those skilled in the art of shaped glass analysis in light of the teachings herein. Therefore, applicants submit that within the scope of the appended claims, the present invention may be practiced otherwise than as specifically described.

What is claimed is:

1. A method of determining glass surface shape comprising:
    providing a rigid horizontal surface on which to position a formed sheet of glass;
    positioning a selectively oriented flat or curved rigid surface of known shape in a predetermined orientation and in a predetermined proximity relative to the horizontal surface on which the formed glass is to be positioned, the selectively oriented surface having a pattern comprising an array of geometric shapes disposed thereon;
    providing at least one source of visible light to illuminate the selectively oriented patterned surface;
    providing an optoelectronic device capable of receiving an optical image and recording a digital image of the optical image, which optoelectronic device is positioned in a predetermined proximity to the rigid horizontal surface and to the selectively oriented patterned surface;
    providing a computer programmed with at least one algorithm capable of analyzing the digitized image received from the optoelectronic device;
    precisely orienting the formed sheet of glass, having at least one major convex surface, on the rigid horizontal surface relative to the selectively oriented patterned surface;
    utilizing the optoelectronic device to capture an optical image of the pattern formed on the convex surface of the formed glass sheet as created by the light reflected to the optoelectronic device from the selectively oriented patterned rigid surface and digitizing same to form a digital image of the pattern, wherein any designated location on the pattern is defined by a single digital image; and
    electronically transferring the digital image of the pattern on the surface of the formed glass sheet to the computer, wherein, for any designated location on the pattern, the single digital image is analyzed by the at least one algorithm to provide a representation of the shape of the convex major surface of the formed glass sheet at that designated location.

2. The method defined in claim 1, wherein the optoelectronic device is a digital camera.

3. The method defined in claim 1, wherein the pattern displayed on the selectively oriented surface comprises a plurality of spatially separated multi-colored geometric shapes disposed on a contrasting background.

4. The method defined in claim 1, wherein the pattern displayed on the selectively oriented surface comprises a plurality of spatially separated black and white geometric shapes.

5. The method defined in claim 1, wherein the horizontal surface is a transport system capable of transporting a plurality of shaped glass sheets in serial fashion such that an image of each glass sheet is captured and analyzed.

6. The method defined in claim 1, wherein the pattern comprises a grid of a predetermined number of multi-colored squares, each square being between 1 mm and 10 mm on a side.

7. The method defined in claim 1, wherein the pattern comprises a grid of a predetermined number of alternating black and white squares, each square being between 1 mm and 10 mm on a side.

8. The method defined in claim 3, wherein the pattern contains a center reference shape.

9. The method defined in claim 8, wherein shapes of differing predetermined colors are adjacent to each of the four sides of the center reference shape.

10. The method defined in claim 6, wherein the at least one algorithm utilizes the pattern to identify at least one specific location on the pattern, which corresponds to a specific location on the formed glass sheet.

11. The method defined in claim 10, wherein the at least one algorithm utilizes the pattern to identify a plurality of locations on the formed sheet glass.

12. The method defined in claim 8, wherein the at least one algorithm identifies the center reference shape as the intersection point of x and y axes.

13. The method defined in claim 9, wherein the at least one algorithm identifies different color shapes as locations on the x and y axes.

14. The method defined in claim 6, wherein the at least one algorithm calculates the inclination of the glass surface in three-dimensional space, at the reflected vertices of the grid pattern.

15. The method defined in claim 10, wherein at least one algorithm calculates the inclination of the glass surface in three-dimensional space, at the centers of a predetermined number of geometric shapes.

16. The method defined in claim 15, wherein the at least one algorithm calculates the rate of change between the centers of adjacent pairs of the geometric shapes in three-dimensional space.

17. The method defined in claim 1, wherein the pattern comprises from 2 to 8 different colors.

18. A method of quantitatively measuring optical distortion in a formed glass sheet comprising:
    providing a rigid horizontal surface on which to position a formed sheet of glass;
    positioning a selectively oriented flat or curved rigid surface of known shape in a predetermined orientation and in a predetermined proximity relative to the horizontal surface on which the formed glass is to be positioned, the essentially selectively oriented surface having a pattern disposed thereon;
    providing at least one source of visible light to illuminate the selectively oriented, rigid patterned surface;
    providing an optoelectronic device capable of receiving an optical image and recording a digital image of the optical image, which optoelectronic device is positioned in a predetermined proximity to the rigid horizontal surface and to the selectively oriented patterned surface;

providing a computer programmed with at least a first algorithm capable of receiving a digitized image from the optoelectronic device;

precisely orienting the formed sheet of glass, having at least one major convex surface, on the rigid horizontal surface relative to the selectively oriented patterned surface;

utilizing the optoelectronic device to capture an optical image of the pattern visible on the convex surface of the formed glass sheet as created by the light reflected into the optoelectronic device from the selectively oriented patterned rigid surface and digitizing same to form a digital image of the pattern, wherein any designated location on the pattern is defined by a single digital image; and electronically transferring the digital image of the pattern on the surface of the formed glass sheet to the computer, wherein, for any designated location on the pattern, the single digital image is analyzed by the first algorithm to provide a representation of the shape of the convex major surface of the formed glass sheet at that designated location;

utilizing the mathematical representation of the shape of the surface of the formed glass sheet in a second algorithm which includes information about: the orientation of the formed glass sheet in three-dimensional space, the orientation of the formed glass sheet relative to a hypothetical surface having a pattern disposed thereon, and the position of a hypothetical observer relative to the representation of the formed glass sheet in three-dimensional space and the hypothetical surface having the pattern disposed thereon, to predict the location and the magnitude of reflected optical distortion in the formed glass sheet.

* * * * *